United States Patent
Mori et al.

(10) Patent No.: US 9,422,361 B2
(45) Date of Patent: Aug. 23, 2016

(54) PROCESS FOR HIGHLY SELECTIVE PURIFICATION OF TWO PLASMA PROTEINS: VON WILLEBRAND FACTOR (VWF) AND FIBRONECTIN (FN)

(75) Inventors: Filippo Mori, Lucca (IT); Ilaria Nardini, Barga (IT); Claudio Farina, Pisa (IT); Claudia Nardini, Lucca (IT)

(73) Assignee: KEDRION S.P.A. (IT)

( * ) Notice: Subject to any disclaimer, the term of this patent is extended or adjusted under 35 U.S.C. 154(b) by 0 days.

(21) Appl. No.: 13/145,038

(22) PCT Filed: Jan. 19, 2010

(86) PCT No.: PCT/IB2010/050230
§ 371 (c)(1),
(2), (4) Date: Jul. 18, 2011

(87) PCT Pub. No.: WO2010/082184
PCT Pub. Date: Jul. 22, 2010

(65) Prior Publication Data
US 2011/0282032 A1  Nov. 17, 2011

(30) Foreign Application Priority Data
Jan. 19, 2009 (IT) ................. FI2009A0007

(51) Int. Cl.
*C07K 14/78* (2006.01)
*C07K 14/755* (2006.01)

(52) U.S. Cl.
CPC ............... *C07K 14/755* (2013.01); *C07K 14/78* (2013.01)

(58) Field of Classification Search
CPC .............................. C07K 14/755; C07K 14/78
See application file for complete search history.

(56) References Cited

U.S. PATENT DOCUMENTS

| 5,252,709 | A | * | 10/1993 | Burnouf et al. | 530/382 |
| 7,166,709 | B2 | * | 1/2007 | Josic et al. | 530/412 |
| 7,985,846 | B2 | * | 7/2011 | Josic et al. | 530/412 |

OTHER PUBLICATIONS

Burnouf-Radosevich, M., et al. 1992 Vox Sang 62: 1-11.*
Laffan, M., et al. 2004 Haemophilia 10: 199-217.*
Mori, F., et al. 2008 Vox Sanguinis 95: 298-307.*
D.E.G. Austen, et al., "Factor VIII Fractionation on Aminohexyl Sepharose with Posible REduction in Hepatitis B Antigen," Thromb Haemostas (Stuttgart), 48:1:46-48 (1982).
Erik Berntorp, et al., "Use of a High-Purity Factor VIII Concentrate (Hemate P) in von Willebrand's Disease1 ," Vox Sang, 56:212-217 (1989).
Eva Engvall et al., "Binding of Soluble Form of Fibroblast Surface Protein, Fibronectin, to Collagen," Int. J. Cancer, 20:1-5 (1977).
M. W. Mosesson, et al., "The Cold-insoluble Globulin of Human Plasma," J. Biol. Chem., 245:21:5728-5736 (1970).
Deane F. Mosher, "Cross-Linking of Cold-insoluble Globulin by Fibrin-stabilizing Factor," J. Biol. Chem., 250:16:6614-6621 (1975).
B. A. Ferret, et al., "Isolation of Small Molecular Forms of Factor VIII/ von Willebrand Factor from Plasma," Haemostasis, 14:289-295 (1984).
Matti Vuento, et al., "Purification of Fibronectin from Human Plasma by Affinity Chromatography under Non-Denaturing Conditions," Biochem. J., 183:331-337 (1979).
Matti Vuento, et al., "Dissociation of Fibronectin from Gelatin-Agarose by Amino Compounds," Biochem. J., 175:333-336 (1978).
L. Winkelman, et al., "Severely Heated Therapeutic Factor VIII Concentrate of High Specific Activity," Vox Sang, 57:97-103 (1989).

* cited by examiner

*Primary Examiner* — Marsha Tsay
(74) *Attorney, Agent, or Firm* — Fish & Tsang, LLP

(57) ABSTRACT

There is described a chromatographic purification process that allows highly purified von Willebrand factor (vWF) and Fibronectin (Fn) to be obtained, starting from a biological fraction enriched in vWF and Fn and easily scaled up to industrial level. Chromatographic purification was obtained by a strong anionic exchange resin. The concentrates obtained have a high specific activity and, given the low content of contaminant proteins, are particularly suitable for therapeutic use.

16 Claims, 1 Drawing Sheet

Multimers of vWF :

a) plasma;   b) 0.22M di NaCl fraction;   c) 0.60M di NaCl fraction a)    b)    c)

SDS-PAGE in non reducing conditions.

1: Standard High range unstained;    2: starting material 0,16 M ;
3: intermediate 0,22 M ;              4-5: eluate 0,60 M (W2).

PROCESS FOR HIGHLY SELECTIVE PURIFICATION OF TWO PLASMA PROTEINS: VON WILLEBRAND FACTOR (VWF) AND FIBRONECTIN (FN)

RELATED APPLICATIONS

This application is a §371 of PCT/IB2010/050230 filed Jan. 19, 2010, and claims priority from Italian Patent Application No, FI2009A000007 filed Jan. 19, 2009, both incorporated by reference in their entirety.

FIELD OF THE INVENTION

The present invention relates to the field of purification of proteins from human plasma.

STATE OF THE ART

The von Willebrand Factor (vWF) is one of the largest known glycoproteins that circulates in plasma. This protein is in the form of multimers, held together by disulfide bridges, the molecular weight of which can vary from 260 KDa (base subunit) up to 20 million Daltons.

The vWF is very important in the haemostatic process; in fact, besides performing its function as carrier and stabilizer of FVIII in the blood, it is essential for the adhesion of thrombocytes to damaged endothelium/subendothelium. In the first step of haemostasis, adhesion, the vWF acts by forming a bridge between the specific receptors of the surface of the thrombocytes (GpIb, GpIIb/IIIa) and the components of the endothelium.

Changes in the levels of vWF can cause serious bleeding problems. Von Willebrand Disorder (vWD) is an autosomic hereditary disorder of the blood prevalent in around 0.8% and is principally caused by deficiency or by abnormal multimeric composition of the vWF. Consequently, FVIII coagulation (FVIII:C) activity is often reduced, as the vWF cannot perform its FVIII stabilizing function. Patients who suffer from vWD can show symptoms similar to those of haemophilia A, caused by a decrease in the half-life of FVIII.

The relevance of the vWF for platelet adhesion to the damaged endothelium is reflected in the fact that patients with vWD often have a high bleeding time; therefore, the principal object of vWD treatment is the correction of bleeding time and of FVIII deficiency.

There are currently two therapeutic approaches to the disease: 1) the use of desmopressin (1-deamine-8-D-arginine vasopressin or DDAVP) and 2) replacement therapy with infusion of plasma concentrates containing vWF. Treatment with DDAVP, which, stimulates the release of endogenous vWF from endothelial cells, is the therapy of choice, but in many cases patients with vWD do not respond to this treatment or become refractory after repeated administrations, and therefore it becomes necessary to resort to the use of concentrates obtained from plasma (cryoprecipitates or FVIII/vWF concentrates). However cryoprecipitates are not without risk of viral contamination, as they are not subject to an effective viral inactivation step and the excess of contaminating proteins, not useful for the patient, can cause adverse reactions. On the contrary, although FVIII/vWF complex concentrates are subjected to effective viral inactivation/removal treatments, the purification process and the concentrates obtained have been optimised for treating patients with Haemophilia A and not those suffering from von Willebrand disease. In fact, highly purified FVIII/vWF concentrates have been developed for haemophilic patients (as described, for example, in WO 01/79260 and in WO2008135568), either containing a low vWF content or in which the FVIII content in relation to the vWF is so high that it can increase the risk of thrombosis in patients suffering from vWD (especially in subclass 2N and 3). For these patients, who have normal plasma concentrations of FVIII, vWF, concentrates containing negligible levels of FVIII are instead more suitable.

Fibronectin is another glycoprotein with high molecular weight (440 KDa) which exists in two forms: one soluble in plasma and one insoluble.

This protein has a determining role in some physiological functions of extreme importance for homeostasis of the organism.

In particular, it interacts with cell migration and differentiation, nerve regeneration, revascularization and repair of epithelial, mucosal or endothelial lesions. Fn is capable of stimulating, as non-specific opsonin, phagocytosis of the macrophage system. Deficiency of this protein is accompanied by a reduction of phagocytic activity which, in the case of an infection, can lead to an increase in mortality. It has therefore been hypothesized that the administration of exogenous fibronectin can have a therapeutic effect in serious clinical conditions, characterized by low haematic levels of this glycoprotein and by the propensity to evolve towards multiple vital organ failure, such as the liver, kidneys, lungs, etc. These conditions are represented by sepsis, coagulopathies, extensive burns, intensive-surgical procedures.

Another use of Fn in therapy is linked to the capacity of this protein to promote neovascularization, epidermal cell migration through granulation tissue and reorganization of the basal membrane of epithelial cells and of the mucosa. Fn therefore plays an important role in the closure of epithelial and mucosal lesions and, for example if applied as eye drops, can accelerate reepithelisation and repair of corneal lesions caused by, traumas or by infections.

Recognition of the potential therapeutic effect of vWF and Fn have greatly increased interest in these proteins and efforts to obtain highly purified vWF and Fn that respond to therapeutic needs and to market requirements.

Purification of proteins such as vWF and Fn is very difficult due to their high molecular weigh and their adhesive properties, which compromise recovery and can cause their deterioration.

Both vWF and Fn have been purified separately using plasma as starting material or enriched fractions such as cryosupernatant or intermediates deriving from precipitation pretreatments and/or chromatography of the cryoprecipitate.

Berntorp et al. (Vox Sang. 1989, 56: 212) and Winkelman et al. (Vox Sang: 1989, 57:97) for example purify vWF from plasma by differential precipitation in the presence of glycine or sodium sulphate. Perret et al. (Haemostasis 1984, 14:289) and Austen et al. (Thromb. Haemostas. 1982; 48:46 48) instead purify vWF from plasma using different chromatography separation methods, such as molecular exclusion or anion exchange. However, all these techniques produce vWF with poor yields and low purity.

The U.S. Pat. No. 6,579,723 describes a process for preparing highly purified vWF by immunoaffinity chromatography with anti-vWF antibodies. However, the addition of a subsequent affinity chromatography step does not help to totally eliminate the presence of residual antibodies that can cause immunological reactions.

The U.S. Pat. No. 5,408,039, starting from a fraction enriched in vWF and subjected to viral activation, provides for two subsequent chromatographies, the first on Fractogel DEAE TSK 650 and the second on gelatin-Sepharose to eliminate fibronectin, considered an impurity; instead, the U.S. Pat. No. 5,252,709 substitutes the latter chromatography with gel filtration on Sephacryl S-400.

The patent US 2006/0036081, starting from an enriched fraction obtained from a preceding chromatography step on DEAE-Fractogel TSK 650, purifies vWF, eliminating Fn impurities with a chromatography on DEAE-Fractogel TSK 650 using a buffer (sodium Acetate 20 mM) with high flow velocities.

The patent EP0469985B1, starting from virus inactivated cryoprecipitate, purifies vWF by means of two chromatography steps on the same type of resin, which in this case is Q-Sepharose FF; the method uses in the second chromatography an ion force buffer that allows vWF to bind, purifying it from proteins such as fibrinogen, IgG, fibronectin, albumin, which do not bind to the resin.

Instead, in relation to Fn, Mosesson & Umfleet, (1970; J. Biol. Chem. 245, 5728-5736); Mosher, D. F. (1975; J. Biol. Chem. 250, 6614-6621) purify it from plasma combining precipitation step, molecular exclusion chromatography and anion exchange chromatography. However, these are very lengthy processes, with very low yields and which cannot easily be scaled up. Vuento A. & Mosher D. (1978, Biochem J. 175, 33-336) purify Fn with immunoaffinity chromatography, while Engvall & Ruoslahti (1977, Int. J. Cancer. 20, 1-5) purify it with gelatin affinity chromatography. However; these methods appear to have denaturation effects on the protein.

Vuento M. & Vaheri (1979, Biochem. J. 183, 331-337) improved the first affinity chromatography on gelatin Sepharose and added a further affinity chromatography: arginine Sepharose. However, this process is also very lengthy and difficult to scale up to industrial level.

All the methods devised to date for the preparation of both vWF and Fn are difficult to adapt to industrial scale and often produce proteins with low purity and/or partially deteriorated and instable; in any case, no method provides for the purification of both proteins in a sequential manner.

The object of the present invention is therefore to provide a simple method with high yield and efficiency, easily scaled up to industrial level, to sequentially obtain with the same process the two well-characterized concentrates based on the proteins of interest, vWF and Fn, with a high degree of purification and stability, suitable for their therapeutic use.

DEFINITIONS AND ABBREVIATIONS

Ag: antigen
CBA: collagen binding activity
Fn: fibronectin
Ig: immunoglobulin
RCo: Ristocetin cofactor
TMAE-trimethylammoniumethyl
TNBP: tri-n-butyl-phosphate
IU: international units
VWD: von Willebrand Disease
vWF: von Willebrand Factor

SUMMARY OF THE INVENTION

The present invention provides a simple process, with high yield and efficiency, easy to adapt to industrial level for the production of two concentrates containing essentially vWF and Fn, starting from a biological fraction enriched in vWF and Fn, characterized by only one chromatographic purification on strong anionic exchange resin.

The concentrates obtained have high specific activity and, given the low content of contaminant proteins, are particularly suitable for therapeutic use.

DETAILED DESCRIPTION OF THE INVENTION

Figure 1:
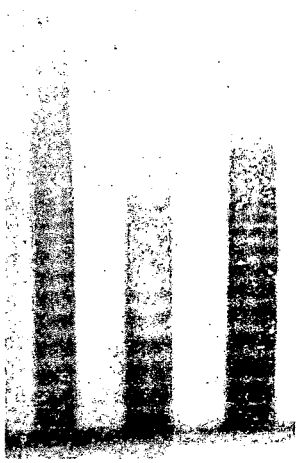
FIG. 1-Multimer distribution of vWF purified by electrophoresis in 1.5% agarose gel.

The present invention relates to a process for the sequential production of two highly purified proteins: vWF and Fn, starting from a biological fraction enriched in, vWF and Fn, characterized by only one chromatographic purification on strong anionic exchange resin.

In accordance with the present invention, biological fraction enriched in vWF and Fn is intended as a fraction deriving from a precedent purification treatment by anion exchange chromatography performed according to known methods on human plasma, cryoprecipitate or other plasma fraction optionally subjected to a treatment of pre-purification, such as adsorption on aluminium hydroxide and optionally subjected to viral inactivation with the solvent/detergent method (Tween/TNBP).

According to a particularly preferred and advantageous aspect, said enriched biological fraction is a waste fraction of the FVIII productive process.

The chromatographic separation of the present invention can be performed on strong anionic exchange resins, such as Q Sepharose™ (GE Healthcare), UNOsphere Q™ (Bio Rad Laboratories Inc.), Toyopearl® Super Q and Toyopearl® GigaCap Q (TOSOH), and preferably on resins composed of a synthetic hydrophilic medium with tentacle structure containing long polymer chains, bound at the end of which are positively charged groups suitable for, strong anionic exchange (such as TMAE—trimethylammoniumethyl); examples of resins of this type are Fractoprep® EMD TMAE or Fractogel® EMD TMAE (Merck).

The use of tentacle resins promotes binding of high molecular weight proteins (>300 KDa) or adhesive proteins such as vWF, decreasing interaction with the matrix, which could cause a decrease in protein recovery and/or its inactivation. According to the present invention, the only one chromatographic purification is characterized by an appropriate sequential increase of the saline concentration which allows elimination of contaminant proteins and sequential elution of two solutions respectively containing Fn and vWF with excellent purity and yield.

According to the present invention, the chromatographic purification preferably comprises the following steps:

a) conditioning of the strong anionic exchange resin with an aqueous buffer having pH comprised between 6.8 and 7.4, containing NaCl at a concentration between 0.10 and 0.15M and optionally comprising glycine and/or $CaCl_2$;
b) charging the fraction enriched in the proteins of interest;
c) eluting the contaminant proteins using the conditioning buffer;
d) eluting a solution containing Fn with a buffer at pH between 6.8 and 7.4 containing NaCl at concentration comprised between 0.2 and 0.27 M and wherein $CaCl_2$ is optionally present in concentration comprised between 1 and 5 mM;

e) eluting a solution containing vWF with a buffer at pH between 6.8 and 7.4 containing NaCl at concentration comprised between 0.6 and 1.0 M and wherein $CaCl_2$ is optionally present in concentration comprised between 1 and 5 mM.

Said buffer at pH comprised between 6.8 and 7.4 is obtained, for example, by glycine, citrate, phosphate or Tris.

The solutions obtained containing Fn or vWF were separately ultrafiltered, concentrated and lyophilized.

With this method two highly purified concentrates with excellent stability can be obtained:
- vWF concentrate to be used both for those subclasses of vWD in which the FVIII, content is in a normal range and for those patients for whom the use of desmopressin is not possible;
- an Fn concentrate for systemic use in preventing vital organ failure in conditions of sepsis and/or for topical use as promoter of the repair of epithelial or mucosal lesions.

This method makes it possible to purify the two proteins of therapeutic interest, starting from a waste fraction of the FVIII productive process, thus improving the use of a precious material such as human plasma.

The purification method of the present invention, besides allowing highly purified vWF and Fn concentrates to be obtained, is also efficient, reproducible, can be scaled up to industrial level and provides a product with high yields. The Fn and vWF products obtained have high specific activity, with low concentrations of the principal contaminants, such as fibrinogen, fibronectin, IgG, IgM. The vWF obtained by the present chromatographic process has a multimeric pattern with high percentages of high molecular weight multimers and in particular the present chromatographic process results in an enrichment of high molecular weight multimers in the end product (FIG. 1).

For better understanding of the invention, an example of purification of the two proteins Fn and vWF according to the process of the present invention is set down below.

EXPERIMENTAL PART

Example 1

Purification of vWF and Fn Starting from Cryoprecipitate

After dissolution of 65 g of cryoprecipitate in 10 volumes of $H_2O$, aluminium hydroxide at pH 6.5 at a temperature of 15° C. was added to the solution. After centrifugation the supernatant was subjected to a viral inactivation step with the addition of solvent and detergent (Tween/TNBP) and subsequently loaded on a Toyopearl 650M resin conditioned with 10 mM citrate buffer at pH 7.0 and with a concentration of NaCl of 0.12 M.

The contaminant proteins were eliminated by washing with the same buffer.

Subsequently, by treating the resin with 10 mM citrate buffer at pH 7.0 with 0.16M NaCl, a fraction enriched in vWF and Fn was obtained.

This fraction was dialyzed against a buffer, with a concentration of NaCl of 0.11M and concentrated 2.5 times.

The concentrate was subsequently loaded on a Fractogel EMD TMAE resin, conditioned with 10 mM citrate buffer at pH 7.0 and with a concentration of NaCl of 0.11M. After eliminating any contaminant proteins with the same buffer, the Fn was separated by eluting at a concentration of NaCl of 0.22M. The eluate containing Fn was diafiltered and concentrated against 0.05M Tris buffer, 0.1M NaCl at pH 7.5 until reaching a protein concentration of 5 mg/ml, then sterile filtered, bottled and lyophilized.

The vWF was subsequently eluted increasing the NaCl concentration up to 0.60 M and obtaining a highly purified product.

The eluate containing vWF was diafiltered and concentrated against 10 mM citrate buffer, 0.1M NaCl, 0.12M glycine, 1 mM $CaCl_2$ at pH 7.0 until reaching a concentration of 1000 IU of vWF:Ag/ml; the solution thus obtained was then sterile filtered, bottled and lyophilized.

Distribution of vWF and Fn in the various chromatographic steps is summarized below in Table A.

TABLE A

Distribution of the vWF and fibronectin content in the various fractions of the chromatographic process

| Sample | vWF:Ag (tot U) | recovery (%) | Fibronectin (tot mg) | recovery (%) |
|---|---|---|---|---|
| Enriched fraction | 3325 | — | 447.8 | — |
| 0.22M | 186.9 | 5.6 | 448.2 | 100 |
| 0.60M | 2944 | 88.5 | — | — |

Example 2 vWF Characterization

The product obtained after chromatographic elution with 0.60M NaCl was characterized evaluating the total protein content, vWF:RCo (Ristocetin cofactor) activity and vWF:CBA (Collagen binding activity). Table B below shows their values, while FIG. 1 shows the distribution of vWF multimers present in the chromatographic fractions compared to that present in the plasma, evaluated on 1.5% agarose gel.

TABLE B

Activity and Proteins of the product eluted at 0.60M NaCl

| | |
|---|---|
| vWF:Ag (IU/ml) | 33.00 |
| vWF:RCo (IU/ml) | 20.77 |
| vWF:CBA (IU/ml) | 18.06 |
| Proteins (mg/ml) | 0.198 |
| Specific activity (IU/ml) | 104.8 |
| vWF:RCo/vWF:Ag | 0.63 |
| vWF:CBA/vWF:Ag | 0.55 |

The principal contaminant proteins were evaluated on the product obtained after chromatographic elution with 0.60M NaCl. The results are set down in Table C below:

TABLE C

Concentration of the principal contaminant proteins in a bottle of 1000 IU of vWF:Ag

| Analysis/bottle | Concentration |
|---|---|
| vWF:Ag (IU) | 1000 |
| vWF:RCo (IU) | 582 |
| Proteins (mg) | 6.0 |
| IgG (mg) | <0.005 |
| IgA (mg) | <0.00036 |
| IgM (mg) | 0.033 |
| Fibronectin (mg) | N.D. |
| Fibrinogen (mg) | N.D. |
| FVIII:C (IU) | 48 |

Example 3

Fibronectin Characterization

Figure 2:
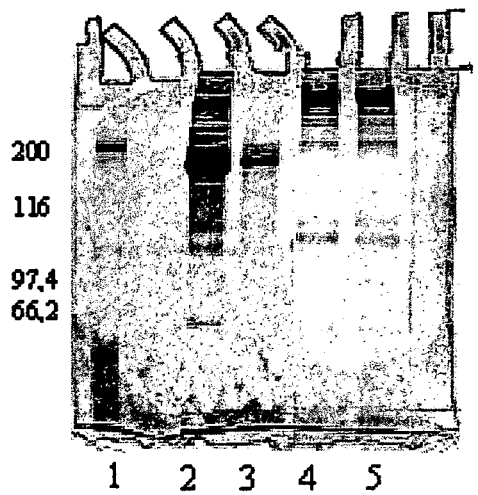
FIG. 2-Electrophoretic pattern of the chromatography fractions in 5% polyacrylamide gel.

The product obtained after chromatographic elution with 0.22M NaCl was characterized evaluating the total protein content, the fibronectin content by nephelometry and the principal polluting proteins. Table D below shows their values while FIG. 2 (line 3) shows the fibronectin purity, evaluated on SDS-PAGE electrophoresis at 5%.

TABLE D

| Characteristics of the product eluted at 0.22M NaCl | |
|---|---|
| Fn:Ag (mg) | 546.4 |
| Proteins (mg) | 541.3 |
| Purity | >95% |
| IgG | 0.3% |
| IgA | N.D. |
| IgM | N.D. |

N.D. not detectable

The invention claimed is:

1. A process for sequential production of (a) a first concentrate consisting essentially of fibronection (Fn) and (b) a second concentrate consisting essentially of von Willebrand Factor (vWF) comprising:
   (i) purifying a human plasma cryoprecipitate containing FVIII, Fn and vWF on an anion exchange chromatographic resin to obtain a plasma fraction enriched in Fn and vWF and poor in FVIII, said plasma fraction enriched in Fn and vWF being a waste fraction of a process for isolating Factor VIII (FVIII) from plasma;
   (ii) sequentially separating Fn and vWF by subjecting said plasma fraction enriched in vWF and Fn to only one subsequent chromatographic purification, wherein the one subsequent chromatographic purification is on strong anionic exchange resin,
   (a) eluting a first concentrate consisting essentially of Fn from said strong anionic exchange resin with a first elution buffer having an ionic strength suitable for obtaining said first concentrate consisting essentially of Fn, and
   (b) then eluting a second concentrate consisting essentially of vWF from said strong anionic exchange resin using a second elution buffer having an ionic strength stronger than said first elution buffer for obtaining said second concentrate consisting essentially of vWF.

2. The process of claim 1, further comprising pre-purifying said human plasma cryoprecipitate via aluminum hydroxide adsorption.

3. The process of claim 2, further comprising subjecting said human plasma cryoprecipitate to viral inactivation after aluminum hydroxide adsorption and before step (i).

4. The process of claim 1, wherein said strong anionic exchange resin comprises a synthetic hydrophobic tentacle type support containing long polymer chains having trimethylaminoethyl (TMAE) groups at their ends.

5. The process of claim 1, wherein:
   (ii)(a) said first elution buffer is a buffer having a pH of from 6.8 to 7.4 and a concentration of NaCl of from 0.2 to 0.27 M, and
   (ii)(b) said second elution buffer is a buffer having a pH of from 6.8 to 7.4 and a concentration of NaCl of from 0.6 to 1.0 M.

6. The process of claim 5, further compromising eluting any contaminant proteins with an aqueous conditioning buffer having a pH of from 6.8 to 7.4 and a concentration of NaCl of from 0.10 to 0.15 M, before directly eluting said first concentrate consisting essentially of Fn.

7. The process of claim 5, further comprising conditioning said strong anionic exchange resin with an aqueous conditioning buffer having a pH of from 6.8 to 7.4 and a concentration of NaCl of from 0.10 to 0.15 M prior to (ii) subjecting said plasma fraction enriched in vWF and Fn to said strong anionic exchange resin.

8. The process of claim 5, wherein said first elution buffer further comprises $CaCl_2$ at a concentration of from 1 to 5 mM.

9. The process of claim 6, wherein said second elution buffer further comprises $CaCl_2$ at a concentration of from 1 to 5 mM.

10. The process of claim 7, wherein said first and second buffers further comprise $CaCl_2$ at a concentration of from 1 to 5 mM.

11. The process of claim 6, wherein said aqueous conditioning buffer contains at least one of $CaCl_2$ and glycine.

12. The process of claim 7, wherein said aqueous conditioning buffer contains at least one of $CaCl_2$ and glycine.

13. The process of claim 1, wherein said anion-exchange chromatographic resin is a weak anion-exchange resin.

14. The process of claim 13, wherein said plasma fraction enriched in Fn and vWF and poor in FVIII is eluted from said weak anion-exchange resin with an elution buffer having a pH of 7.0 of and a concentration of NaCl of 0.16 M.

15. The process of claim 14, further comprising washing said weak anion-exchange resin with a conditioning buffer having a pH of 7.0 and a concentration of NaCl of 0.12 M to eliminate any contaminant proteins, prior to eluting said plasma fraction enriched in Fn and vWF.

16. The process of claim 15, further comprising, prior to washing, loading said human plasma cryoprecipitate containing FVIII, Fn and vWF on said weak anion-exchange resin previously conditioned with the conditioning buffer having a of 7.0 and a concentration of NaCl of 0.12 M.

* * * * *